(12) United States Patent
Mackles

(10) Patent No.: US 7,022,740 B2
(45) Date of Patent: Apr. 4, 2006

(54) LUBRICIOUS OPHTHALMIC SOLUTIONS

(76) Inventor: Leonard Mackles, 311 E. 23rd St., New York, NY (US) 10010

( * ) Notice: Subject to any disclaimer, the term of this patent is extended or adjusted under 35 U.S.C. 154(b) by 0 days.

(21) Appl. No.: 10/835,449

(22) Filed: Apr. 29, 2004

(65) Prior Publication Data

US 2005/0245618 A1    Nov. 3, 2005

(51) Int. Cl.
*A61F 2/00* (2006.01)
*A61K 33/22* (2006.01)
*A61K 47/00* (2006.01)
*A61K 47/30* (2006.01)

(52) U.S. Cl. .................. 514/772.2; 424/427; 424/659; 514/772

(58) Field of Classification Search ............... 424/427, 424/659, 78.04, 660; 514/659, 78.04, 660
See application file for complete search history.

(56) References Cited

U.S. PATENT DOCUMENTS

| | | | |
|---|---|---|---|
| 3,697,575 A | 10/1972 | Naarmann | |
| 4,066,541 A | 1/1978 | Sando | |
| 4,331,781 A | 5/1982 | Zimmerman | |
| 5,234,968 A | 8/1993 | Debus | |
| 5,290,774 A | 3/1994 | Morita | |
| 5,342,620 A | 8/1994 | Chowhan | |
| 5,505,953 A * | 4/1996 | Chowhan | 424/427 |
| 5,597,559 A | 1/1997 | Olejnik | |
| 6,319,464 B1 | 11/2001 | Asgharian | |
| 6,583,124 B1 | 6/2003 | Asgharian | |

FOREIGN PATENT DOCUMENTS

| | | |
|---|---|---|
| CN | 1101364 | 4/1995 |
| JP | 54150468 | 11/1979 |
| JP | 12368866 | 10/1986 |
| WO | WO 9318764 | 9/1993 |

* cited by examiner

*Primary Examiner*—Thurman K. Page
(74) *Attorney, Agent, or Firm*—Omri M Behr

(57) ABSTRACT

There are provided lubricious ophthalmic solutions having a pH of between about 7.0 and about 8.0, consisting essentially of an aqueous solution of from about 0.5–4% by weight of a monographed polyol, borate calculated as the borate equivalent of 20–100% by weight of boric acid relative to said polyol, from about 0.1 to about 1.00% by weight of monographed polysorbate, a monographed preservative and a buffer. Suitably the polyol is polyvinyl alcohol In addition to polyvinyl alcohol (hereinafter PVA) the solution may include other monographed polymers as well as monographed pharmacologically active substances.

21 Claims, No Drawings

LUBRICIOUS OPHTHALMIC SOLUTIONS

FIELD OF THE INVENTION

Discussion of the Prior Art

The use of ophthalmic solutions for relief of many eye conditions is well known in the art. The problem with many of these solutions is that while they are pH compatible with tears, their level of lubricity or slipperiness is less than would be desirable. Thus many advantages of such solutions and the pharmacologically active substances which they may carry are not optimized. A further legal issue which must be met, at least in the United States of America is that the Food and Drug administration has set forth a list of substances which can be used in such non-prescription solutions and no others are permissible. These substances are referred to in the art as "monographed". Thus any invention in this art must be limited to the use of monographed components The cross-linking gelation effect of alkaline borates on polyvinyl Alcohol is well known and documented. The literature is full of warnings about the problems of gelation. Kirk-Othmer in the "Concise Encyclopedia of Chemical Technology 1985", page 1228 states that "as little as 0.1% borax, based on solution weight can cause thermally irreversible gelation". Calvin E. Schildknecht in his book "Vinyl and Related Polymers", John Wiley & Sons, 1952, pages 352–353 lists Borax as an active gelling agent at room temperature for highly hydrolyzed polymers of PVA. The Dupont Co. in their product guide to Elvanol (PVA) products, 1990, Page 11 cautions that borax should be avoided because it causes gelation. The same caution to avoid the gelatinizing agents, boric acid and borax, is contained in the Japanese company, Nippon Gohsei's product guide to their PVA, 2001, page 18.

The Chai et al U.S. Pat. No. 4,255,415 of Mar. 10, 1981 illustrates the use of this gelation mechanism in producing a polyvinyl alcohol ophthalmic gel. Asgharian in U.S. Pat. No. 6,583,124 B2 of Jun. 24, 2003 is quoted as saying in Column 2, lines 16–19 that the Chai gels are "preformed and hard to disperse".

SUMMARY OF THE INVENTION

The surprising finding of this invention is that contrary to the teachings of the prior art, a monographed polyol, suitably polyvinyl alcohol, when cross linked with borate and buffered into the pH range of 7.0–8.0, becomes highly lubricious and does not gel, provided this procedure is carried out in the presence of a polyethylene sorbitan monoester (hereinafter "polysorbate") which is a monographed substance. A further point to be taken into account is that at present there is only one substance suitably monographed as a preservative, and that is benzalkonium chloride. In the system of this invention there is no interference between the preservative and the solution provided by the invention because of the presence of the polyethylene sorbitan monoester.

The basis of the invention is to provide an aqueous solution of a polyol which is moderately cross linked with borate. The polyol is dissolved in water to bring the solution into the range of about 0.5 to about 4% wt, polysorbate is added, if desired with other modifiers or preservatives, the source of borate added and the mixture buffered into the desired range of pH7.0–8.0, the normal pH of the eye being 7.4.

There are provided lubricious ophthalmic solutions having a pH of between about 7.0 and about 8.0, consisting essentially of an aqueous solution of from about 0.5–4% by weight of a monographed polyol, borate calculated as the borate equivalent of 20–100% by weight of boric acid relative to said polyol, from about 0.1 to about 1.00% by weight of monographed polysorbate and a buffer.

Suitably the polyol is polyvinyl alcohol, the polysorbate may be selected from the group consisting of the monolaurate, monopalmitate, monostearate and monooleate of polyethylene 20 sorbitan. The solution may desirably further contain a monographed preservative suitably benzalkonium chloride. In addition to polyvinyl alcohol (hereinafter PVA) the solution may include other monographed polyols as well as monographed pharmacologically active substances.

The process of preparing a solution as described above comprises the steps of dissolving the polyol in water, adding the polysorbate, and thereafter adding dilute aqueous borate solutions, suitably from about 0.5 to about 10% by weight, most suitably 1–3%, preferably about 2% by weight, selected from at least one member of the group consisting of borax and boric acid, adding a buffer to buffer the pH to the desired range and adding water to adjust the concentration to the desired range.

The process of may additionally comprise adding a further monographed polyol to said solution as well as adding a monographed pharmacologically active substance prior to the addition of borate

DESCRIPTION OF THE PREFERRED EMBODIMENTS

The preferred polyol is polyvinyl alcohol, suitably having the formula $(C_2H_4O)_n$ in which the n value lies between 500–5000 and a hydrolysis value=71–89, preferably: 85–89. The initial 4% wt aqueous solution should have a viscosity of 3.0–56.0 mPas(CP), the preferred range: being 40–46. The final range being about 0.5 to about 4% wt preferably 0.75–1.50%

The PVA can be used in combination with other monographed polymers such as; povidone, sodium carboxymethyl cellulose, hydroxymethyl cellulose, hydroxypropyl cellulose and the like. Other polyols that may be also additionally used are those such as glycerin, propylene glycol, polyethylene glycol, and the like.

Useful polysorbates include Polysorbate 20 (polyethylene 20 sorbitan monolaurate, Polysorbate 40 (polyethylene 20 sorbitan monopalmitate), Polysorbate 60 (polyethylene 20 sorbitan monostearate) and Polysorbate 80, (polyethylene 20 sorbitan monooleate) Most preferred is Polysorbate 80 as 0.10–1.00% wt of total solution, preferably 0.20–0.40%. Besides its use as a moderator for controlling the gelation of PVA and alkaline borates, it also protects the benzalkonium chloride against precipitation by the anionic borate PVA.

As source of borate there may be used boric acid N.F. 20–100% of PVA wt., preferably 30–60% of PVA wt. or borax, suitably carrying 10M of water of hydration, in amount 10–80% of PVA wt. preferably 20–40% of PVA wt. Where boric acid is used as the cross linking agent, borax may additionally be used as the buffer, or vice versa.

Other buffers include acetic acid, hydrochloric acid, phosphoric acid, potassium bicarbonate, potassium tetraborate, potassium hydroxide, (0.01–0.2% wt, preferably 0.04–0.10%) potassium carbonate, potassium citrate, potassium phosphate, sodium acetate, sodium bicarbonate, sodium biphosphate, sodium borate, sodium carbonate, sodium citrate, sodium hydroxide(0.01–0.2% wt. preferably 0.04–0.10%), and sodium phosphate Any monographed active which is soluble in the solutions may be used. These include ophthalmic vasoconstrictors such as: ephedrine HCl, naphazoline HCl, phenylephrine HCl, tetrahydrozoline HCl and oxymetazoline HCl, and the like, as well as other monographed actives such as antihistamines As stated above benzalkonium chloride suitably about 0.01 to about 0.1, preferably about 0.01 to about 0.15% wt of total solution may be used as a preservative, which may be potentiated by EDTA.

By mixing the solubilized polymer containing the polysorbate, with mixtures of dilute boric acid solutions or sodium hydroxide or potassium hydroxide solutions, there is formed a controlled cross-linked reaction with the polyvinyl alcohol which now becomes anionic and at the same time exhibits this unique slipperiness and lubricity. The PVA does not gel but remains in solution with little or no increase in viscosity or gelation.

In a preferred procedure the polymer is solubilized by heating and mixing 2.00% wt in water at 80° C. until the mixture is clear and uniform. The controlled cross-linking is formed by slowly adding a dilute solution of boric acid followed by Polysorbate suitably Polysorbate 80 and next a dilute solution of borax, or other suitable buffer in order to bring the total pH of the system to between 7.0 and 8.0. Additional water is added to bring the concentration of the polymer to 1.00% wt. As soon as the pH approaches 7.0 the solution becomes very slippery. The effect will continue past pH 8.0. Since the pH of the fluid in the eye is 7.4, the pH of the system should be kept below 8.0 to prevent eye damage.

Alternatively it is possible to form a cross-linked controlled reaction of PVA and alkaline borate in situ.

In this mode, to a solution of PVA, is added a dilute solution of boric acid followed by Polysorbate 80. Then there is slowly added a solution of sodium hydroxide or potassium hydroxide to form the alkaline borate which in turn cross-links with the PVA. The pH is controlled so that it falls between 7 and 8. The physical effect is the same as if there was used a mixture of boric acid and borax. The solution becomes slippery and lubricious as the pH approaches 7.0.

The system is also very useful in products for contact lens wearers. It will refresh and moisten the lenses and help to remove particulate matter that may cause irritation and discomfort. PVA lowers surface tension and wets out the surface of contact lenses.

EXAMPLE #1

| EYE CARE LUBRICANT | | |
|---|---|---|
| | % | % Actives |
| 1. PVA (2% Solution) | 50.00 | 1.00 |
| 2. Boric acid N.F. (2% Soln.) | 15.00 | 0.30 |
| 3. Borax, 10 M. $H_2O$ (2% Soln.) | 10.00 | 0.20 |
| 4. Disodium EDTA | 0.10 | 0.10 |
| 5. P.E.G. 400 | 1.00 | 1.00 |
| 6. Polysorbate 80 | 0.20 | 0.20 |
| 7. Benzalkonium Cl (1% Soln.) | 1.00 | 0.01 |
| 8. D.I. $H_2O$ | 22.70 | 97.19 |
| | 100.00 | 100.00 | pH = 7.38

Note:
all solutions (indicated as "Soln") in this and following examples are aqueous solutions.

Procedure:
1. Mix #1 and #8 and when uniform add #2 while mixing.
2. Add #4, #5, and #6 to the batch and mix until all are dissolved.
3. Add #7 to the batch and mix.
4. Slowly add #3 to the batch while mixing.
5. Adjust the pH with NaOH or HCl.

EXAMPLE #2

| EYE CARE LUBRICANT WITH TETRAHYDROZOLINE HCl | | |
|---|---|---|
| Actives | % | % |
| 1. PVA (2% Solution) | 50.00 | 1.00 |
| 2. Boric acid N.F. (2% Soln.) | 15.00 | 0.30 |
| 3. Borax, 10 M. $H_2O$ (2% Soln.) | 10.00 | 0.20 |
| 4. Tetrahydrozoline HCl | 0.05 | 0.05 |
| 5. Disodium EDTA | 0.10 | 0.10 |
| 6. P.E.G. 400 | 1.00 | 1.00 |
| 7. Polysorbate 80 | 0.20 | 0.20 |
| 8. Benzalkonium chloride (1.0% Soln.) | 1.00 | 0.01 |
| 9. D.I. $H_2O$ | 22.25 | 97.14 |
| | 100.00 | 100.00 | pH = 7.40

Procedure:
1. Mix #1 and #9 and when uniform, add #2 while mixing.
2. Add #4 to the batch and mix until dissolved.
3. Add #5, #6 and #7 to the batch and mix until dissolved.
4. Add #8 to the batch and mix.
5. Slowly add #3 to the batch with mixing.
6. Adjust the pH with NaOH or HCl.

EXAMPLE #3

| EYE CARE LUBRICANT WITH OXYMETAZOLINE HCl | | |
|---|---|---|
| Actives | % | % |
| 1. PVA (2% Solution) | 50.00 | 1.00 |
| 2. Boric Acid N.F. (2% Soln.) | 15.00 | 0.30 |
| 3. Borax, 10 M. $H_2O$. (2% Soln.) | 10.00 | 0.20 |
| 4. Oxymetazoline HCl | 0.05 | 0.05 |
| 5. Disodium EDTA | 0.10 | 0.10 |
| 6. P.E.G. 400 | 1.00 | 1.00 |
| 7. Polysorbate 80 | 0.20 | 0.20 |

EYE CARE LUBRICANT WITH OXYMETAZOLINE HCl — continued

| Actives | % | % |
|---|---|---|
| 8. Benzalkonium chloride (1.0% Soln.) | 1.00 | 0.01 |
| 9. D.I. H$_2$O | 22.25 | 97.14 |
|  | 100.00 | 100.00 | pH = 7.40

Procedure:
See Example #2.

Procedure:
See Example #2.

EXAMPLE #4

EYE CARE LUBRICANT
In Situ Method

| Actives | % | % |
|---|---|---|
| 1. PVA (2% Solution) | 50.00 | 1.00 |
| 2. Boric acid N.F. (2% Soln.) | 30.00 | 0.60 |
| 3. Disodium EDTA | 0.10 | 0.10 |
| 4. P.E.G. 400 | 1.00 | 1.00 |
| 5. Polysorbate 80 | 0.20 | 0.20 |
| 6. Benzalkonium chloride (1.0% Soln.) | 1.00 | 0.01 |
| 7. NaOH (10% Soln.) | 0.80 | 0.08 |
| 8. D.I. H$_2$O | 16.90 | 97.01 |
|  | 100.00 | 100.00 | pH = 7.60

Procedure:
Alkaline Borate Formed In Situ
1. Mix #1 and #8 and when uniform, add #2 while mixing.
2. Add #3, #4, and #5 to the batch and mix until dissolved.
3. Add #6 to the batch and mix.
4. Slowly add #7 to the batch while mixing to form the alkaline borates.
5. Adjust the pH with NaOH or HCl.

EXAMPLE #5

EYE CARE LUBRICANT With TETRAHYDROZOLINE HCl
In Situ Method

| Actives | % | % |
|---|---|---|
| 1. PVA (2% Solution) | 50.00 | 1.00 |
| 2. Boric acid N.F. (2% Soln.) | 30.00 | 0.60 |
| 3. Tetrahydrozoline HCl | 0.05 | 0.05 |
| 4. Disodium EDTA | 0.10 | 0.10 |
| 5. P.E.G. 400 | 1.00 | 1.00 |
| 6. Polysorbate 80 | 0.20 | 0.20 |
| 7. Benzalkonium chloride (1.0% Soln.) | 1.00 | 0.01 |

EYE CARE LUBRICANT With TETRAHYDROZOLINE HCl — continued
In Situ Method

| Actives | % | % |
|---|---|---|
| 8. NaOH (10% Soln.) | 0.80 | 0.08 |
| 9. D.I. H$_2$O | 16.85 | 96.96 |
|  | 100.00 | 100.00 | pH = 7.24

Procedure:
Alkaline Borate Formed In Situ
1. Mix #1 and #9 and when uniform, add #2 while mixing.
2. Add #3 to the batch and mix until dissolved.
3. Add #4, #5 and #6 to the batch and mix until dissolved.
4. Add #7 to the batch and mix.
5. Slowly add #8 to batch while mixing to form the alkaline borates.
6. Adjust the pH with NaOH or HCl.

EXAMPLE #6

EYE CARE LUBRICANT WITH OXYMETAZOLINE HCl
In Situ Method

| Actives | % | % |
|---|---|---|
| 1. PVA (2% Solution) | 50.00 | 1.00 |
| 2. Boric Acid N.F. (2% Soln.) | 30.00 | 0.60 |
| 3. Oxymetazoline HCl | 0.05 | 0.05 |
| 4. Disodium EDTA | 0.10 | 0.10 |
| 5. P.E.G. 400 | 1.00 | 1.00 |
| 6. Polysorbate 80 | 0.20 | 0.20 |
| 7. Benzalkonium Chloride (1.0% Soln.) | 1.00 | 0.01 |
| 8. NaOH (10% Soln.) | 0.80 | 0.08 |
| 9. D.I. H$_2$O | 16.85 | 96.96 |
|  | 100.00 | 100.00 | pH = 7.30

Procedure:
Alkaline Borate Formed In Situ
See Example #5

EXAMPLE #7

EYE CARE LUBRICANT WITH POTASSIUM BORATE
In Situ Method

| Actives | % | % |
|---|---|---|
| 1. PVA (2% Solution) | 50.00 | 1.00 |
| 2. Boric acid N.F. (2% Soln.) | 30.00 | 0.60 |
| 3. Disodium EDTA | 0.10 | 0.10 |
| 4. P.E.G. 400 | 1.00 | 1.00 |
| 5. Polysorbate 80 | 0.20 | 0.20 |
| 6. Benzalkonium chloride (1.0% Soln.) | 1.00 | 0.01 |
| 7. KOH (10% Soln.) | 0.90 | 0.09 |
| 8. D.I. H$_2$O | 16.80 | 97.00 |
|  | 100.00 | 100.00 | pH = 7.40

Procedure:
Alkaline Borate Formed In Situ
See Example #4

I claim:

1. A lubricious ophthalmic solution having a pH of between about 7.0 and about 8.0, consisting essentially of:
from about 0.5–4% by weight of a monographed polyol,
borate calculated as the borate equivalent of 20–100% by weight of boric acid relative to said polyol,
from about 0.1 to about 1.00% by weight of monographed polysorbate,
the monograph permitted amount 0.1 wt of monographed preservative a buffer and water to 100% wt.

2. The solution of claim 1 wherein the polyol is polyvinyl alcohol.

3. The solution of claim 2 wherein the polysorbate is selected from the group consisting of the mono laurate, monopalmitate, monostearate and monooleate of polyethylene 20 sorbitan.

4. The solution of claim 3 wherein the preservative is benzalkonium chloride at about 0.01 to about 0.015% wt.

5. The solution of claim 2 further comprising other monographed polyols.

6. The solution of claim 3 further comprising other monographed polyols.

7. The solution of claim 2 further comprising monographed pharmacologically active substances.

8. The solution of claim 3 further comprising monographed pharmacologically active substances.

9. The solution of claim 4 further comprising monographed pharmacologically active substances.

10. The solution of claim 6 further comprising monographed pharmacologically active substances.

11. The solution of claim 7 further comprising monographed pharmacologically active substances.

12. A process of preparing a solution of claim 1 comprising the steps of a) dissolving the polyol in water,
b) adding a dilute solution of borate selected from at least one member of the group consisting of borax and boric acid,
c) adding the polysorbate,
d) adding monographed preservative
e) adjusting the pH to the desired range and
f) adding water to adjust the concentration to the desired range.

13. The process of claim 12, wherein the steps are carried out in the sequence of (a), (c), (d), (b), (e–f).

14. The process of claim 12, wherein the order of the steps is (a), (d), (c), (b), (e–f).

15. The process of claim 12 wherein the borate is borax only.

16. The process of claim 12 wherein the borate is boric acid only.

17. The process of claim 12 wherein the borate is borax and boric acid.

18. The process of claim 12 additionally comprising adding a further monographed polyol to said solution.

19. The process of claim 12 further comprising adding a monographed pharmacologically active substance prior to the addition of borate.

20. The process of claim 13 further comprising adding a monographed pharmacologically active substance prior to the addition of borate.

21. The process of claim 12 further comprising adding a monographed preservative prior to the addition of borate.

* * * * *